United States Patent [19]
Tamborski et al.

[11] 4,120,863
[45] Oct. 17, 1978

[54] FLUORINE-CONTAINING BENZOXAZOLES

[75] Inventors: Christ Tamborski; John B. Christian, both of Dayton, Ohio

[73] Assignee: The United States of America as represented by the Secretary of the Air Force, Washington, D.C.

[21] Appl. No.: 837,329

[22] Filed: Sep. 27, 1977

[51] Int. Cl.$^2$ .......................................... C07D 263/56
[52] U.S. Cl. ............................. 260/307 D; 252/392; 252/403; 260/453 RW; 260/575; 568/709; 568/775
[58] Field of Search .................................. 260/307 D

[56] References Cited

U.S. PATENT DOCUMENTS

| | | | |
|---|---|---|---|
| 3,564,003 | 2/1971 | Burton et al. | 260/307 |
| 3,565,908 | 2/1971 | Burton et al. | 260/307 |

OTHER PUBLICATIONS

Braz et al. (I) – C.A. 67, 116836q (1967).
Simonov et al. – C.A. 77, 74375 (1972).
Evers et al. – C.A. 84, 17775p (1976), and pp. 969 CS and 970 CS of vol. 84 Chem. Substance Index.
Braz et al. (II) – C.A. 63, 5622 (1965).

*Primary Examiner*—Raymond V. Rush
*Attorney, Agent, or Firm*—Joseph E. Rusz; Cedric H. Kuhn

[57] ABSTRACT

Benzoxazoles substituted in the 2-position with a perfluoroalkylether radical and bis-benzoxazoles in which the 2-position carbon atoms of the benzoxazole rings are attached to one another with a perfluoroalkylene or perfluoroalkyleneether radical. The compounds are useful as anti-rust additives in grease formulations based on fluorine-containing fluids.

5 Claims, No Drawings

FLUORINE-CONTAINING BENZOXAZOLES

RIGHTS OF THE GOVERNMENT

The invention described herein may be manufactured or used by or for the Government of the United States for all governmental purposes without the payment of any royalty.

FIELD OF THE INVENTION

This invention relates to benzoxazole compounds which are substituted with various fluorine-containing substituents in various positions of the benzoxazole ring system.

BACKGROUND OF THE INVENTION

Perfluoroalkyl-substituted benzoxazoles have been disclosed by G. I. Braz et al in the Russian journal Khimiya Geterotsiklicheskikh Soedinenii, I, 147 (1965). [Chemical Abstracts, 63, 5622 (1965).] Two compounds were reported in which two perfluoroalkyls, namely, $CF_3$ and $C_3F_7$, were substituted in the 2-position. Both of these compounds are relatively low boiling fluids ($CF_3$ = 62° C./19 mm; $C_3F_7$ = 85° C./22 mm) and have comparatively high vapor pressures. As a result, the compounds would have limited practical value for high temperature applications requiring low volatility.

Compounds similar to those described in the preceding paragraph in that they disclose benzoxazole systems substituted with $C_3F_7$ radicals are described in the patent literature. Thus, 2,2'-bis(heptafluoropropyl)-5,5'-bibenzoxazole is disclosed in U.S. Pat. No. 3,564,003 while 2,2'-bis(heptafluoropropyl)-6,6'-bibenzoxazole is disclosed in U.S. Pat. No. 3,565,908. These compounds are high boiling materials having low vapor pressures that are stated to be useful as anti-plasticizers.

It is an object of this invention to provide fluorine-containing benzoxazoles which have a low volatility.

Another object of the invention is to provide benzoxazoles substituted with perfluoroalkyl and perfluoroalkylether radicals.

A further object of the invention is to provide bis-benzoxazoles in which the 2-position carbon atoms are attached to one another with a perfluoroalkylene or a perfluoroalkyleneether radical.

Still another object of the invention is to provide low volatility benzoxazoles which are useful as anti-rust agents for grease formulations based on fluorine-containing greases.

Other objects and advantages of the invention will become apparent to those skilled in the art upon consideration of the accompanying disclosure.

SUMMARY OF THE INVENTION

The present invention resides in benzoxazole compounds having the following structural formula:

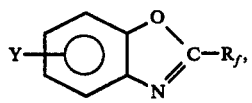

wherein $R_f$ is perfluoroalkyl, perfluoroalkylether, or

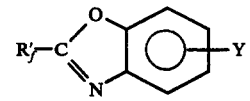

in which $R_f'$ is perfluoroalkylene or perfluoroalkyleneether, and Y is perfluoroalkyl, perfluoroalkylether or hydrogen, Y being hydrogen only when $R_f$ is perfluoroalkylether or

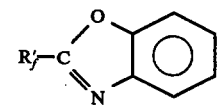

The benzoxazole compounds of this invention are prepared by reacting 2-aminophenol or a substituted 2-aminophenol with a perfluoroalkyl or perfluoroalkylether imidate ester or a perfluoroalkylene or perfluoroalkyleneether diimidate ester. The reaction involved in preparing a compound with a single benzoxazole ring can be represented by the following equation:

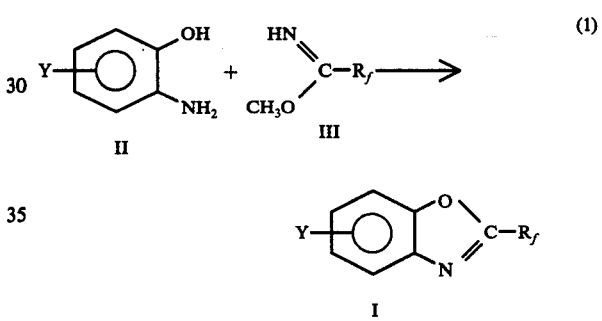

In synthesizing compounds of this invention containing two benzoxazole rings, the reaction shown by the following equation is conducted:

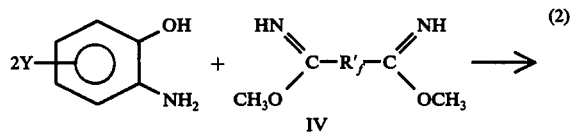

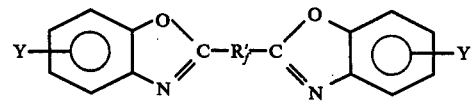

In the foregoing equations, $R_f$, $R_f'$ and Y are as defined hereinabove.

The reactions illustrated by equations (1) and (2) are conducted in the presence of glacial acetic acid, utilizing hexafluoroisopropanol as the reaction medium. The reaction temperature usually ranges from about 45° to 50° C. Depending upon the structure of the particular imidate ester utilized, the reaction time generally varies from about 10 minutes to 5 or 6 days. The sterically hindered imidate esters require longer periods of time as compared to the nonhindered imidate esters.

As seen from equations (1) and (2), the $R_f$ and $R_f'$ are derived from the imidate esters (III) and the diimidate esters (IV). These imidate esters are well known compounds that are described in the literature. For example, following the procedure described by H. C. Brown and C. R. Wetzel in Journal of Organic Chemistry, 30, 3724 (1965), a variety of imidate esters can be synthesized from a variety of fluorine-containing nitriles. Also, the synthesis of perfluoroalkyleneether diimidate esters is disclosed by one of us in U.S. Pat. No. 4,011,255. Examples of $R_f$ groups include perfluoroalkyls such as $C_xF_{2X+1}$, where $x$ is an integer from 1 to 10, inclusive; and perfluoroalkylethers such as $CF_2(OCF_2CF_2)_yOC_2F_5$ where y is zero or an integer from 1 to 10, inclusive; and $CF(CF_3) [OCF_2CF(CF_3)]_zOC_3F_7$, where z is zero or an integer from 1 to 10 inclusive. Examples of $R_f'$ groups include perfluoroalkylenes such as $(CF_2)_a$, where a is an integer from 1 to 10, inclusive; $(CF_2)_4O(CF_2)_4O(CF_2)_4$; and $Z[CF(CF_3)-CF_2O]_n(CF_2)_4[OCF_2CF(CF_3)]_nZ$, where each Z is $(CF_2)_4O$ or $CF(CF_3)OCF_2-CF_2O$, and $n$ is an integer from 1 to 5, inclusive.

Also, as seen from equations (1) and (2), the source of the Y groups is the substituted 2-aminophenol (II) [When Y is hydrogen, 2-aminophenol is used as the reactant with the imidate ester (III) or diimidate ester (IV).] As mentioned previously, Y can be a perfluoroalkyl or a perfluoroalkylether and examples of these radicals are set forth in the preceding paragraph.

The 2-aminophenols (II) can be synthesized by following a nitration and reduction procedure as described by R. C. Evers, Abstracts, 167th National Meeting of the American Chemical Society, Los Angeles, CA., April 1974, No. Poly. 087. The process for preparing the compound in which the Y group is in the para position can be represented by the following equation:

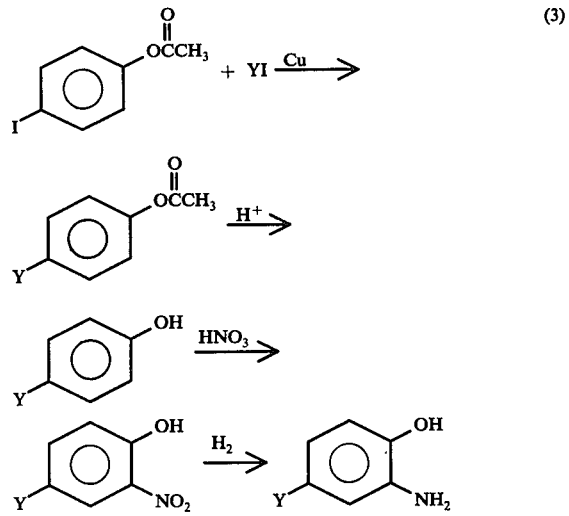

(3)

In the foregoing equation (3), Y is perfluoroalkyl or perfluoroalkylether. By utilizing m-$IC_6H_4OC(O)CH_3$ or o-$IC_6H_4OC(O)CH_3$ as a starting material, 2-aminophenols can be prepared in which the Y group is in the meta or ortho positions. It is often preferred to use 2-amino-4-perfluoropropylphenol as the substituted 2-aminophenol, i.e., where Y is $C_3F_7$.

A more comprehensive understanding of the invention can be obtained by referring to the following illustrative examples which are not intended, however, to be unduly limitative of the invention.

EXAMPLE I

Synthesis of Imidate Esters (a) $C_3F_7O[CF(CF_3)CF_2O]_2CF(CF_3)C(=NH)OCH_3$ About 0.1 g of sodium was dissolved in anhydrous $CH_3OH$ (50 ml). To this solution was added $C_3F_7O[CF(CF_3)CF_2O]_2CF(CF_3)CN$ (24.6 g; 0.038 mole), and the mixture was stirred at room temperature for 3.5 hours. The reaction mixture was then hydrolyzed with water, the lower organic layer was separated, and the aqueous layer was extracted with $CCl_2FCF_2Cl$. The extracts and the lower organic layer were combined, dried ($MgSO_4$) and aspirated, yielding the crude product (25.6 g). Distillation yielded the pure imidate ester product (24.7 g; 96% yield), b.p. 86° C./15 mm.

Analysis Calc'd for $C_{13}H_4F_{23}NO_4$: C,23.13; H,0.60; H,2.07% Found: C,23.15; H,0.69; N,2.24% Molecular weight (mass spectroscopy): Calc'd - 675 Found - 675. The infrared and nuclear magnetic resonance spectra were consistent with the imidate ester structure. (b) Following the same procedure described in (a) above, $C_3F_7C(=NH)OCH_3$ (b.p. 74° C.; 81% yield); $C_2F_5O(CF_2)_2OCF_2C(=NH)OCH_3$ (b.p. 109° C.; 79% yield); $C_3F_7O[CF(CF_3)O]_4CF(CF_3)C(=NH)OCH_3$ (b.p. 108° C./2 mm; 90% yield); and $CH_3O(NH=)C(CF_2)_8C(=NH)OCH_3$ (b.p. 80° C./0.2 mm; 85% yield) were prepared.

EXAMPLE II

Synthesis of 2-amino-4-perfluoropropylphenol

A mixture of p-$IC_6H_4OC(O)CH_3$ (19.7 g; 0.075 mole), n-$C_3F_7I$ (33.5 g; 0.113 mole), copper bronze (12.60 g; 0.2 g atom) and dimethylsulfoxide (200 ml) were placed in a glass reactor (Fischer-Porter reactor) and heated with stirring for 6 hours in a 125° C. oil bath. After cooling, the reaction mixture was filtered, hydrolyzed with water and extracted three times with diethyl ether. The combined ether extracts were dried ($MgSO_4$) and aspirated, yielding a liquid (22 g, 96% yield). Gas chromatographic analysis indicated a single component, namely, p-$C_3F_7C_6H_4OC(O)CH_3$.

A solution of p-$C_3F_7C_6H_4OC(O)CH_3$ (33.2 g; 0.14 mole) in $CH_3OH$ (200 ml) containing concentrated HCl (20 ml) was heated to reflux for 24 hours. After cooling and aspiration of the solvent, a brown liquid resulted (28.4 g; 99% crude yield). A gas chromatographic analysis indicated primarily one major component. Distillation provided the product p-$C_3F_7C_6H_4OH$ (26.2 g; 92% yield).

Analysis Calc'd for $C_9H_5F_7O$: C,41.2; H,1.92% Found: C,41.3; H,1.95% Molecular weight (mass spectroscopy): Calc'd - 262 Found - 262.

A solution of glacial $CH_3CO_2H$ (26 ml) containing concentrated $HNO_3$ (3.6 ml) and p-$C_3F_7C_6H_4OH$ (5.0 g; 0.019 mole) was heated at 37° C. for 4 hours. The reaction was cooled and hydrolyzed with water (200 ml). The mixture was extracted three times with diethyl ether, the ether fractions dried ($MgSO_4$) and aspirated. Distillation yielded the product 2-nitro-4-perfluoropropylphenol (4.9 g; 84% yield), b.p. 49° C./0.25 mm.

Analysis Calc'd for $C_9H_4F_7NO_3$: C,35.2; H,1.31; N,4.56% Found: C,35.2; H,1.03; H,4.56% Molecular weight (mass spectroscopy): Calc'd - 307 Found - 307.

To a cooled, deoxygenated solution of the above perfluoropropylnitrophenol (33.8 g; 0.11 mole) dissolved in $C_2H_5OH$ (250 ml) was added concentrated HCl (25 ml) and platinum on carbon (2 g of a 10% Pt-C). The reactor was flushed with hydrogen and then maintained at a pressure of 50 psi. Shaking of the reactor was maintained for 24 hours. The catalyst was filtered and the filtrate aspirated to dryness. The resulting solid was dissolved in water (700 ml), neutralized with $NaHCO_3$ and extracted with diethyl ether and dried ($MgSO_4$). Aspiration of the ether yielded a solid (33.7 g) which on recrystallization from deoxygenated heptane yielded the product 2-amino-4-perfluoropropylphenol (24.3 g; 80% yield), m.p. 116°–118°.

Analysis Calc'd for $C_9H_6F_7NO$: C39.0; H,2.18; N,5.05% Found: C,39.1; H,2.29; N,5.00% Molecular weight (mass spectroscopy): Calc'd: 277 Found: 277.

The infrared and nuclear magnetic resonance spectra of all the above intermediates and the desired product were consistent with their structures.

EXAMPLE III

Synthesis of 2-$C_3F_7O[CF(CF_3)CF_2O]_2CF(CF_3)$-benzoxazole

A mixture of o-$NH_2C_6H_4OH$ (1.09 g; 0.01 mole), $C_3F_7O[CF(CF_3)CF_2O]_2$-$CF(CF_3)C(=NH)OCH_3$ (6.75 g; 0.01 mole), glacial $CH_3CO_2H$ (1.14 ml; 0.02 mole) and hexafluoroisopropanol (30 ml) was heated with stirring in an oil bath at 48° C. Periodically, a sample was removed and analyzed by gas chromatography. The maximum conversion to the product was attained in 5 days. The reaction was hydrolyzed with water and the resulting lower organic layer was separated. The aqueous layer was extracted with $CCL_2FCF_2Cl$ and the extracts combined with the lower organic layer and dried ($MgSO_4$). The solvent was removed by aspiration and the remaining material distilled to yield and product (6.50 g; 88% yield), b.p. 72°/0.07 mm.

EXAMPLES IV–VIII

In these examples runs were conducted in which other benzoxazoles of this invention were prepared following the method described in Example III. In the runs, imidate esters synthesized as described in Example I were utilized. 2-Aminophenol and 2-amino-4-perfluoropropylphenol were used in the reactions. The reaction times for maximum yields varied with the rate of cyclization. The sterically hindered imidate esters required 5 to 6 days whereas with some of the non-hindered imidate esters cyclizations were completed within 10 minutes. The $R_f$ and Y groups of the reactants and the benzoxazole products as well as pertinent data for the runs (including the run of Example III) are set forth hereinafter in the Table.

TABLE

| Ex.[1] No. | $R_f$ | Y | B.P./m.m. | M.S.[2] (found) | Analysis (Calc'd/Found) C | H | N |
|---|---|---|---|---|---|---|---|
| III | $CF(OCF_2CF)_2OC_3F_7$ with $CF_3$, $CF_3$ | H | 72°/0.07 | M⁺ 735 | 29.41 / 29.08 | 0.55 / 0.46 | 1.91 / 2.12 |
| IV | $C_3F_7$ | $C_3F_7$ | 96°/8 | M⁺ 455 | 34.28 / 34.40 | 0.66 / 0.53 | 3.08 / 3.09 |
| V | $CF_2O(CF_2)_2OC_2F_5$ | H | 76°/8 | M⁺ 419 | 34.38 / 34.36 | 0.96 / 1.10 | 3.34 / 3.32 |
| VI | $CF(OCF_2CF)_2OC_3F_7$ with $CF_3$, $CF_3$ | $C_3F_7$ | 95°/0.03 | M⁺ 903 | 27.92 / 28.14 | 0.33 / 0.66 | 1.55 / 1.72 |
| VII | $CF(OCF_2CF)_4OC_3F_7$ with $CF_3$, $CF_3$ | H | 123°/0.02 | M⁺ 1067 | 27.01 / 27.03 | 0.38 / 0.41 | 1.31 / 1.67 |
| VIII | bis-benzoxazole $(CF_2)_8$ bridge | H | m.p. 117–119° | M⁺ 636 | 41.54 / 41.59 | 1.27 / 1.08 | 4.41 / 4.53 |

[1] Isolated yields were 70–95%; G. C. yields were ~ 100% in most preparations; N.M.R. and I.R. data were consistent with structures.
[2] M.S. (mass spectral) analyses were performed by chemical ionization techniques.

As seen from the foregoing, the present invention provides benzoxazoles substituted with perfluoroalkyl and perfluoroalkylether radicals as well as bis-benzoxazoles in which the 2-position carbon atoms are attached to one another with a perfluoroalkylene or perfluoroalkyleneether radical. The benzoxazole products have high boiling points and low vapor pressures. Thus, by the proper selection of perfluoroalkyl or perfluoroalkylether substituents on the benzoxazole ring, a variety of fluorine-containing benzoxazoles, either solid or liquid, can be obtained that have characteristic high boilding points and very low vapor pressures.

The benzoxazoles are particularly useful as anti-rust agents. Thus, when incorporated into fluorine-containing greases, the compounds inhibit rusting of metal components in contact with the greases.

As will be evident to those skilled in the art, modifications of the present invention can be made in view of the foregoing disclosure that fall within the spirit and scope of the invention.

We claim:

1. A fluorine-containing benzoxazole having the following structural formula:

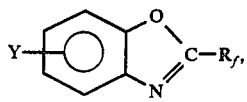

wherein $R_f$ is $C_xF_{2x+1}$, where $x$ is an integer from 1 to 10, inclusive; $CF_2(OCF_2CF_2)_yOC_2F_5$, where $y$ is zero or an integer from 1 to 10, inclusive; $CF(CF_3)[OCF_2CF(CF_3)]_zOC_3F_7$, where $z$ is zero or an integer from 1 to 10, inclusive; or

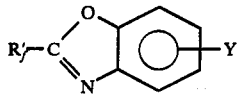

where $R_f'$ is $(CF_2)_4O(CF_2)_4O(CF_2)_4$ or $Z[CF(CF_3)CF_2O]_n(CF_2)_4[OCF_2CF(CF_3)]_nZ$, where each Z is $(CF_2)_4O$ or $CF(CF_3)OCF_2CF_2O$, and $n$ is an integer from 1 to 5, inclusive; and Y is $C_xF_{2x+1}$, where $x$ is an integer from 1 to 10, inclusive; $CF_2(OCF_2CF_2)_yOC_2F_5$, where $y$ is zero or an integer from 1 to 10, inclusive; $CF(CF_3)[OCF_2CF(CF_3)]_zOC_3F_7$, where $z$ is zero or an integer from 1 to 10, inclusive; or hydrogen, $R_f$ being $C_xF_{2x+1}$ only when Y is other than hydrogen.

2. A fluorine-containing benzoxazole having the following structural formula:

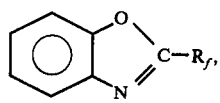

wherein $R_f$ is $CF_2(OCF_2CF_2)_yOC_2F_5$, where $y$ is zero or an integer from 1 to 10, inclusive; or $CF(CF_3)[OCF_2CF(CF_3)]_zOC_3F_7$, where $z$ is zero or an integer from 1 to 10 inclusive.

3. The fluorine-containing benzoxazole of claim 2 in which $R_f$ is $CF_2O(CF_2)_2OC_2F_5$.

4. The fluorine-containing benzoxazole of claim 2 in which $R_f$ is $CF(CF_3)[OCF_2CF(CF_3)]_2OC_3F_7$.

5. The fluorine-containing benzoxazole of claim 2 in which $R_f$ is $CF(CF_3)[OCF_2CF(CF_3)]_4OC_3F_7$.

* * * * *